United States Patent [19]

Varma

[11] Patent Number: 4,488,995

[45] Date of Patent: Dec. 18, 1984

[54] ANDROSTENE-17β-ALKYLTHIOMETHYL ETHERS

[75] Inventor: Ravi K. Varma, Belle Mead, N.J.

[73] Assignee: E. R. Squibb & Sons, Inc., Princeton, N.J.

[21] Appl. No.: 577,444

[22] Filed: Feb. 6, 1984

[51] Int. Cl.³ .............................. C07J 1/00; C07J 7/00
[52] U.S. Cl. ................................................. 260/397.45
[58] Field of Search ..................................... 260/397.45

[56] References Cited

U.S. PATENT DOCUMENTS 4,232,015 11/1980 Teutsch et al. ..................... 424/243
4,330,541 5/1982 Annen et al. .................... 260/397.45

OTHER PUBLICATIONS

Fitzner et al., "J.A.C.S.", vol. 87–No. 28, pp. 5670–5678.
Steroids, vol. 38, p. 651.

Primary Examiner—Elbert L. Roberts
Attorney, Agent, or Firm—Lawrence S. Levinson; Donald J. Barrack

[57] ABSTRACT

Antiinflammatory activity is exhibited by steroids having the structural formula

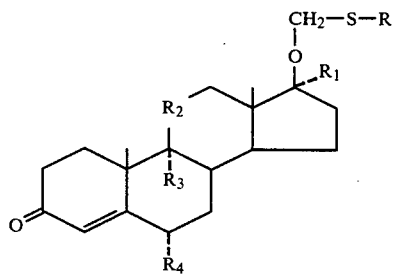

or a 1,2-dihydro derivative thereof, wherein
R is alkyl;
$R_1$ is hydrogen, alkyl, alkenyl, alkynyl, or aryl;
$R_2$ is carbonyl or β-hydroxymethylene;
$R_3$ is hydrogen or halogen; and
$R_4$ is hydrogen, methyl or fluorine.

13 Claims, No Drawings

ANDROSTENE-17β-ALKYLTHIOMETHYL ETHERS

BACKGROUND OF THE INVENTION

U.S. Pat. No. 4,232,015, issued Nov. 4, 1980, discloses antiinflammatory steroids having the partial structural formula

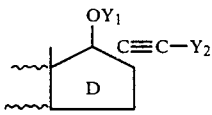

wherein $Y_1$ is an acyl residue of a carboxylic acid having 1 to 18 carbons or carbonic acid, and $Y_2$ is alkyl of 1 to 12 carbons (optionally unsaturated), trifluoromethyl, aryl or arylalkyl.

U.S. Pat. No. 4,330,541, issued May 18, 1982, discloses antiinflammatory steroids having the partial structural formula

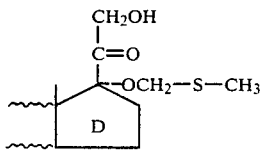

*Steroids*, 38:651 (1981) discloses an antiinflammatory steroid having the partial structural formula

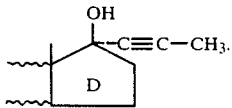

SUMMARY OF THE INVENTION

Steroids having the formula

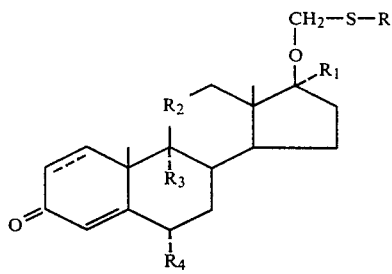

have antiinflammatory activity. In formula I, and throughout the specification, the symbols are as defined below.

R is alkyl;
$R_1$ is hydrogen, alkyl, alkenyl, alkynyl, or aryl;
$R_2$ is carbonyl or β-hydroxymethylene;
$R_3$ is hydrogen or halogen; and
$R_4$ is hydrogen, methyl or fluorine.

The dotted lines in the 1,2-position of the structural formulas shown in this specification indicate the optional presence of ethylenic unsaturation.

The term "aryl", as used throughout the specification either individually or as part of a larger group, refers to phenyl or phenyl substituted with one, two or three alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

The terms "alkenyl" and "alkynyl", as used throughout the specification either individually or as part of a larger group, refer to groups having 2 to 13 carbon atoms.

DETAILED DESCRIPTION OF THE INVENTION

The steroids of formula I, and the 1,2-dehydro and 6,7-dehydro derivatives thereof, are topical antiinflammatory agents that can be used to treat skin conditions such as dermatitis, psoriasis, sunburn, eczema, neurodermatitis, or anogenital pruritus, and inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma the topical antiinflammatory steroids of this invention may be administered in the conventional manner, e.g., as solid medicament which has been atomized. U.S. Pat. Nos. 3,948,264 and 4,147,166 are exemplary of the literature which describes devices that can be used to administer solid medicaments for inhalation therapy.

The steroids of formula I can be prepared from the corresponding androstene having the formula

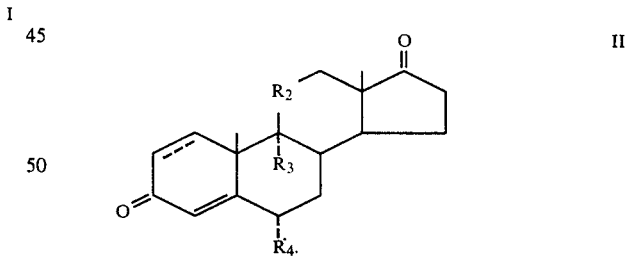

The androstenes of formula II are well known in the art; see, for example, U.S. Pat. No. 4,361,559, issued Nov. 30, 1982.

In the starting steroids of formula II, the 3-oxo substituent is more reactive than the 17-oxo substituent. It is necessary, therefore, to protect the 3-substituent prior to carrying out any reactions to modify the 17-substituent. This can be accomplished using techniques that are well known in the art. For example, a steroid of formula II can be reacted with benzoyl chloride in the presence of an organic base (e.g., pyridine) to yield the corresponding androstene having the formula

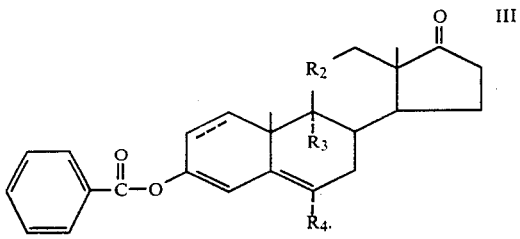

Reaction of a protected androstene of formula III with a compound having the formula

wherein R'₁ is alkyl, alkenyl, alkynyl or aryl, deprotects the 3-oxo substituent as well as reacting with the 17-oxo substituent to yield a compound having the formula

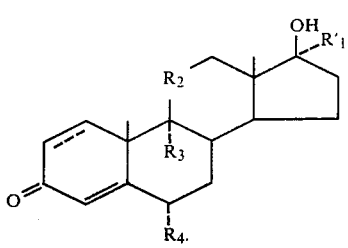

The reaction is preferably run in an organic solvent such as tetrahydrofuran.

Reaction of an androstene of formula IV with a chloromethylalkylsulfide having the formula

in the presence of a hindered tertiary amine base (e.g., diisopropylethyl amine) yields the desired androstenes of formula I wherein R₁ is other than hydrogen.

Alternatively androstenes of formula I wherein R is methyl and R₁ is other than hydrogen can be obtained by reacting an androstene of formula IV with dimethylsulfoxide, acetic anhydride and acetic acid.

The steroids of formula I wherein R₁ is hydrogen can be prepared by first chemically reducing an androstene of formula II (or a corresponding 11β-acetyloxy derivative) using, for example, sodium borohydride. The resulting steroid has the formula

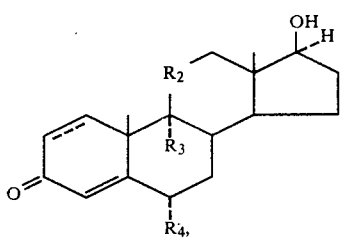

and is produced in admixture with a small amount of its 17α isomer.

An androstene of formula VI (or a mixture containing an androstene of formula VI and its 17α isomer) can be reacted with a chloromethylalkylsulfide of formula V in the presence of a hindered tertiary amine base (e.g., diisopropylethyl amine) to yield the corresponding product of formula I wherein R₁ is hydrogen (or a mixture containing the product and its 17α isomer).

Alternatively, androstenes of formula I wherein R is methyl and R₁ is hydrogen can be obtained by reacting an androstene of formula VI with dimethylsulfoxide, acetic anhydride and acetic acid.

Separation of a steroid of formula VI or formula I (wherein R₁ is hydrogen) from its 17α isomer can be accomplished using art-recognized techniques such as column chromatography.

The following examples are specific embodiments of this invention.

EXAMPLE 1

(11β,17α)-9-Fluoro-11-hydroxy-17-methyl-17-[(methylthio)methoxy]androsta-1,4-dien-3-one

(A)

3-(Benzoyloxy)-9-fluoro-11β-hydroxyandrosta-1,3,5(6)-trien-17-one

9-Fluoro-11β-hydroxyandrosta-1,4-diene-3,17-dione (10.0 g; 0.03 mole), 14.7 ml of distilled benzoyl chloride and 290 ml of dry pyridine were heated together in a pre-flamed flask under nitrogen at 100° C. (oil bath) for 24 hours. The reaction mixture was cooled, treated with methanol (125 ml) and stirred at room temperature for 3 hours. The solution was concentrated to ⅓ of its original volume, poured into 500 ml of 3%. hydrochloric acid and stirred for 10.minutes. The acidic solution was then extracted twice with 500 ml portions of dichloromethane which in turn was washed twice with 500 ml portions of water. The organic solution was dried over anhydrous magnesium sulfate, filtered and stripped to dryness, evaporating the semi-solid obtained several times from toluene. The semi-solid was then triturated with 20 ml of methanol and filtered, washing the solids with a small amount of methanol.

A second run with an additional 10.0 g of starting steroid was worked up in the same manner to give another 8.0 g of crude product. The filtrates were combined, stripped to dryness and the syrup obtained was dissolved in chloroform:ethyl acetate (4:1; 100 ml) and chromatographed on a silica gel column (Woelm; 150 g), quickly eluting the column with chloroform:ethyl acetate (4:1). The fractions containing the desired product were combined, stripped to dryness and triturated with benzene (80 ml) and hexane (70 ml). The solid obtained was triturated further with methanol (20 ml) and filtered. The solids from both runs were combined and dried in vacuo at 60° C. for 2 hours and overnight at room temperature to yield 16.12 g of the title compound with consistent spectra data.

(B)

(11β,17β)-9-Fluoro-11,17-dihydroxy-17-methylandrosta-1,4-dien-3-one 3-(Benzoyloxy)-9-fluoro-11β-hydroxyandrosta-1,3,5(6)-trien-17-one (2.0 g; 4.78 mmole) was dissolved in 140 ml of dry, distilled tetrahydrofuran and cooled to −5° C. to 0° C. The cooled solution was treated dropwise with 13.9 ml of 1.4M methyllithium (4 equivalents) over a period of 15 minutes, and then kept overnight at 0° C.

The reaction mixture was then warmed to room temperature, diluted with water (250 ml) and stirred for 15 minutes. The organic solvent was removed on the rotary evaporator and the precipitate that had formed was filtered off and dissolved in dichloromethane (250 ml).

The filtrate was extracted with dichloromethane (250 ml), both organic solutions were combined and dried over anhydrous magnesium sulfate, filtered and the clear filtrate evaporated to dryness to yield 2.0 g of a syrupy product.

The crude product was dissolved in chloroform:ethyl acetate (4:1; 300 ml), impregnated onto silica gel (20 g) and flash-chromatographed on a silica gel column, (LPS-1) eluting with chloroform:ethyl acetate (4:1; 15.0 liters). The desired fractions were combined and evaporated to dryness to yield 587 mg of impure title compound. A 250 mg portion of the above product was recrystallized by dissolving it in a mixture of methanol:dichloromethane (30 ml; 1:5), concentrating the solution to one-third of its volume and diluting the solution with hexane (50 ml). The crystals that formed on scratching were filtered off and dried overnight in vacuo at 90° C. to yield 208 mg of the title compound, melting point 292°–294° C., $[\alpha]_D^{25} + 38.8°$ (c, 0.08; chloroform). form).

Anal. Calc'd. for $C_{20}H_{27}FO_3$; C, 71.83; H, 8.14; F, 5.68. Found: C, 71.48; H, 8.12; F, 5.70.

(C)

(11β,17α)-9-Fluoro-11-hydroxy-17-methyl-17-[(methylthio)methoxy]androsta-1,4-dien-3-one (11β,17β)-9-Fluoro-11,17-dihydroxy-17-methylandrosta-1,4-dien-3-one (310 mg; 0.9 mmole) was treated with 6.2 ml of acetic anhydride and 3.1 ml of glacial acetic acid in 9.3 ml of dimethylsulfoxide. The reaction mixture was stirred at room temperature for 24 hours under nitrogen after which it was slowly poured in a saturated sodium bicarbonate solution (100 ml) and stirred for 15 minutes. The aqueous suspension was then extracted twice with 150 ml portions of dichloromethane which were in turn washed twice with water (50 ml). The organic extract was dried over anhydrous magnesium sulfate, filtered and the clear filtrate evaporated to dryness to yield 400 mg of crude product.

The crude product was dissolved in chloroform:ethyl acetate (9:1; 10 ml) and flash chromatographed on a silica gel column, (LPS-1) eluting the column with chloroform:ethyl acetate (9:1; 1.5 liters). The fractions containing the desired product were combined and evaporated to dryness to yield 176 mg of impure title compound.

The product was recrystallized from dichloromethane:hexane (35 ml; 1:6), concentrated and the white crystals obtained on scratching were filtered off. Drying overnight in vacuo at 60° C. yielded 146 mg of the title compound, melting point 198°–200° C., $[\alpha]_D^{25} + 51.7°$ (c, 0.35; chloroform).

Anal. Calc'd. for $C_{22}H_{31}FO_3S$: C, 66.97; H, 7.92; F, 4.82; S, 8.13. Found: C, 67.21; H, 8.06; F, 4.80; S, 8.13.

EXAMPLE 2

(11β,17β)-9-Fluoro-11-hydroxy-17-[(methylthio)methoxy]-17-(1-propynyl)androsta-1,4-dien-3-one (A)

(11β,17β)-9-Fluoro-11,17-dihydroxy-17-(1-propynyl)androsta-1,4-dien-3-one

Propynyllithium (97%, 1.06 g, 22.4 mmole) was dissolved in dry, distilled tetrahydrofuran, cooled to 0° C. and treated portionwise under nitrogen with 2.0 g (4.73 mmol) of 3-(benzoyloxy)-9-fluoro-11β-hydroxyandrosta-1,3,5(6)-trien-17-one in 15 ml of dry tetrahydrofuran. The reaction mixture was kept at 0° C. under nitrogen for 40 hours, after which it was warmed to room temperature and treated with water (250 ml). The mixture was stirred for 30 minutes and the tetrahydrofuran removed in the rotary evaporator. The aqueous suspension was extracted twice with 250 ml portions of dichloromethane and the organic extracts were dried over anhydrous magnesium sulfate and filtered. The clear filtrate was then evaporated to dryness to yield 2.4 g of crude title compound.

The crude product mixture was dissolved in chloroform:ethyl acetate (8:1; 25 ml) and flash chromatographed twice to give 296 mg of the desired compound. This was still contaminated with traces of impurities and was chromatographed twice on preparative silica gel plates. The desired band was extracted successively with dichloromethane:ethyl acetate (1:1; 400 ml) and dichloromethane:ethyl acetate (1:9; 400 ml) to yield 210 mg of pure title compound. This was then dissolved in dichloromethane (10 ml) and the solution was diluted with 100 ml of hexane. The resulting suspension was concentrated to one-half its volume and the white precipitates that formed was filtered off and dried for 24 hours in vacuo at room temperature to yield 186 mg of the title compound, melting point 143°–145° C. (shrinking starts from 120° C.), $[\alpha]_D^{25} - 4.0°$ (c, 0.45; chloroform).

Anal. Calc'd. for $C_{22}H_{27}FO_3$: C, 73.72; H, 7.59; F, 5.30. Found: C, 73.71; H, 7.55; F, 4.99.

(B)

(11β,17β)-9-Fluoro-11-hydroxy-17-[(methylthio)methoxy]-17-(1-propynyl)androsta-1,4-dien-3-one (11β,17β)-9-Fluoro-11,17-dihydroxy-17-(1-propynyl)androsta-1,4-dien-3-one (400 mg; 1.2 mmole) was dissolved in 12 ml of dry dimethylsulfoxide, treated with acetic anhydride (8 ml) and glacial acetic acid (4 ml) and stirred at room temperature under nitrogen for 30 hours. The reaction mixture was diluted with water (160 ml) and stirred for one hour. The resulting emulsion was extracted twice with chloroform (175 ml), and the extracts were combined, washed with water (50 ml), dried over anhydrous magnesium sulfate, filtered and the clear filtrate evaporated to dryness. The syrup obtained was chromatographed twice on preparative silica gel plates, developing the plates several times with chloroform:ethyl acetate (9:1). The desired band was cut off and extracted twice with chloroform:ethyl acetate (1:1; 200 ml) to yield 80 mg of pure title compound. This was crystallized from dichloromethane:hexane (1:10) and the white crystals obtained were filtered and dried in vacuo at 75° C. for 4 hours. Yield: 63.4 mg, melting point 203°–205° C., $[\alpha]_{25} + 14.2°$ (c, 0.12; chloroform).

Anal. Calc'd. for $C_{23}H_{31}FO_3S$: C, 68.87; H, 7.47; F, 4.54; S, 7.66. Found: C, 69.13; H, 7.51; F, 4.50; S, 7.39.

EXAMPLE 3

(11β,17β)-9-Fluoro-11-hydroxy-17-[(methylthio)methoxy]androsta-1,4-dien-3-one (A)

(11β,17β)11-(Acetyloxy)-9-fluoro-17-hydroxyandrosta-1,4-dien-3-one

A solution of (11β)-acetyloxy-9-fluoroandrosta-1,4-dien-3-one (10.0 g; 27.75 mmole) in tetrahydrofuran (300 ml) containing water (3.0 ml) was stirred at room temperature and sodium borohydride substituted on silica gel (11.0 g) was added in portions of approximately 4.0 g, 3.0 g, 2.0 g, and 2.0 g every two to three minutes. Gas evolution was noted. After an additional 10 minutes, the mixture was filtered through a bed of Celite and the solids were washed with small amounts of tetrahydrofuran. The solvent was evaporated to afford the title compound as a solid. One crystallization of this from ethyl acetate-hexane gave the analytical specimen (9.3 g), melting point 191°–192° C., $[\alpha]_D^{25} +93.5°$ (c, 0.58; chloroform).

Anal. Calc'd. for $C_{21}H_{27}FO_4$: C, 69.59; H, 7.51; F, 5.24. Found: C, 69.69; H, 7.46; F, 5.30.

(B)

(11β,17β)-11-(Acetyloxy)-9-fluoro-17-[(methylthio)methoxy]androsta-1,4-dien-3-one To a solution of (11β,17β)-11-(acetyloxy)-9-fluoro-17-hydroxyandrosta-1,4-dien-3-one (1.6 g, 4.42 mmole) in dry dimethylsulfoxide (30 ml), acetic acid (10 ml) and acetic anhydride (20 ml) were added. The starting steroid disappeared in 20 hours. The mixture was added into water and was extracted with chloroform (3×100 ml). The chloroform extracts were combined, washed with dilute brine and water, dried (anhydrous magnesium sulfate) and was evaporated in vacuo. The residue was dissolved in chloroform-hexane (1:1) and was absorbed on a column of silica gel (45 g). Elutions of the column successively with the same solvent mixture, chloroform and chloroform-ethyl acetate mixtures (2,3,5 and 10% ethyl acetate) gave (i) the homogeneous (tlc) title compound (1.1 g), (ii) a mixture of the 17α-isomer of the title compound and (11β)-11-(acetyloxy)-9-fluoroandrosta-1,4-dien-3,17-dione (300 mg), and (iii) (11β)-11-(acetyloxy)-9-fluoroandrosta-1,4-dien-3,17-dione (280 mg).

One crystallization of the 1.1 g solid from ethyl acetate-hexane gave the homogeneous analytical specimen (900 mg), melting point 142°–143° C., $[\alpha]_D^{25} +113.0°$ (c, 0.39; chloroform).

Anal. Calc'd. for $C_{23}H_{31}FO_4S$: C, 65.38; H, 7.39; F, 4.50; S, 7.57. Found: C, 65.29; H, 7.40; F, 4.53; S, 7.60.

(C)

(11β,17β)-9-Fluoro-11-hydroxy-17-[(methylthio)methoxy]androsta-1,4-dien-3-one

A solution of (11β,17β)-11-(acetyloxy)-9-fluoro-17-hydroxyandrosta-1,4-dien-3-one (1.0 g, 2.36 mmole) in a mixture of tetrahydrofuran (15 ml) and methanol (15 ml) was stirred under an atmosphere of nitrogen and 3M sodium hydroxide (2.0 ml) was added. After 40 minutes, a *slight* excess of acetic acid was added and the mixture was concentrated in vacuo. The resulting slurry was diluted with water and was extracted with chloroform. The chloroform extract was washed with water, dried (magnesium sulfate anhydrous) and was evaporated to afford the homogeneous (tlc) title compound (850 mg). One crystallization of this from ethyl acetate and drying (110° C., 0.3 mm, 18 hours) gave the analytical specimen (700 mg), melting point 224°–225° C., $[\alpha]_D^{25} +95.9°$ (c, 0.61; chloroform).

Anal. Calc'd. for $C_{21}H_{29}FO_3S$: C, 66.29; H, 7.68; S, 8.43; F, 4.99. Found: C, 66.14; H, 7.61; S, 8.28; F, 5.05.

What is claimed is:

1. A steroid having the formula

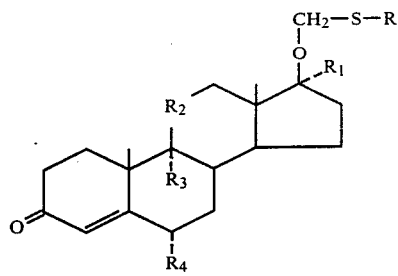

or a 1,2-dehydro derivative thereof, wherein
R is alkyl;
$R_1$ is hydrogen, alkyl, alkenyl, alkynyl, or aryl;
$R_2$ is carbonyl or β-hydroxymethylene;
$R_3$ is hydrogen or halogen; and
$R_4$ is hydrogen, methyl or fluorine.

2. A steroid in accordance with claim 1 having the formula

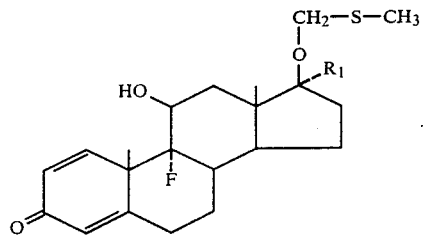

3. A steroid in accordance with claim 1 wherein $R_1$ is hydrogen.

4. A steroid in accordance with claim wherein $R_1$ is alkyl.

5. A steroid in accordance with claim 1 wherein $R_1$ is alkenyl.

6. A steroid in accordance with claim 1 wherein $R_1$ is alkynyl.

7. A steroid in accordance with claim 1 wherein $R_1$ is aryl.

8. A steroid in accordance with claim 1 wherein $R_3$ is halogen.

9. A steroid in accordance with claim 1 wherein $R_3$ is hydrogen.

10. A steroid in accordance with claim 1 wherein $R_4$ is hydrogen.

11. The steroid in accordance with claim 1, (11β,17α)-9-fluoro-11-hydroxy-17-methyl-17-[(methylthio)methoxy]androsta-1,4-dien-3-one.

12. The steroid in accordance with claim 1, (11β,17β)-9-fluoro-11-hydroxy-17-[(methylthio)methoxy]-17-(1-propynyl)androsta-1,4-dien-3-one.

13. The steroid in accordance with claim 1, (11β17β)-9-fluoro-11-hydroxy-17-[(methylthio)methoxy]androsta-1,4-dien-3-one.

* * * * *